United States Patent [19]

Grier et al.

[11] 4,139,559

[45] Feb. 13, 1979

[54] PROCESS FOR PREPARATION OF 1-[1,5-DI-(3,3-DIMETHYLNORBORN-2-YL)-3-PENTYL]-1,5,9-TRIAZANONANE AND NOVEL INTERMEDIATES

[75] Inventors: Nathaniel Grier, Englewood, N.J.; Richard A. Dybas, Center Square, Pa.; Robert A. Strelitz, Edison, N.J.

[73] Assignee: Merck & Co., Inc., Rahway, N.J.

[21] Appl. No.: 869,879

[22] Filed: Jan. 16, 1978

Related U.S. Application Data

[63] Continuation of Ser. No. 702,317, Jul. 2, 1976, abandoned.

[51] Int. Cl.$^2$ ............................................. C07C 87/40
[52] U.S. Cl. ................................................. 260/563 P
[58] Field of Search ...................................... 260/563 P

[56] References Cited

U.S. PATENT DOCUMENTS 4,081,477  3/1978  Hoffmann et al. ............... 260/563 P

*Primary Examiner*—Paul F. Shaver
*Attorney, Agent, or Firm*—Edmunde D. Riedl; Julian S. Levitt

[57] ABSTRACT

A process for preparing 1-[1,5-di-(3,3-dimethylnorborn-2-yl)-3-pentyl]-1,5,9-triazanonane from 1,5-di-(3,3-dimethylnorborn-2-yl)-3-pentanone by reaction with ammonia to form, after reduction, 3-amino-[1,5-di-(3,3-dimethylnorborn-2-yl)pentane]. This latter compound is reacted with acrylonitrile, reduced, and the diamine product again reacted with acrylonitrile and again reduced. Alternative routes wherein the ketone is reduced to the novel alcohol and optionally the novel halide and either then reacted with 3,3'-iminobispropylamine to form the desired polyamine are also shown.

4 Claims, No Drawings

PROCESS FOR PREPARATION OF 1-[1,5-di-(3,3-DIMETHYLNORBORN-2-yl)-3-PENTYL]-1,5,9-TRIAZANONANE AND NOVEL INTERMEDIATES

This is a continuation of application Ser. No. 702,317, filed July 2, 1976, now abandoned.

This invention relates to 1-[1,5-di-(3,3-dimethylnorborn-2-yl)-3-pentyl]-1,5,9-triazanonane and acid addition salts thereof, hereinafter referred to as the alkylated polyamine and its acid addition salts, and particularly novel processes for its preparation.

The polyamine and its salts described herein are excellent broad spectrum antimicrobial agents which are especially effective against gram positive and negative bacteria, particularly the troublesome gram negative of the genus Pseudomonas at aqueous concentrations of 1.0 to 100 ppm. Examples of susceptible species include, inter alia, *Staphylococcus aureus, Streptococcus pyogenes, Bordetella bronchiseptica, Pasteurella multocida, Escherichia coli, Salmonella typhimurium, S. pullorum, Klebsiella pneumoniae, Aerobacter aerogenes, Pseudomonas aeruginosa, Desulfovibrio desulfuricans, Bacillus mycoides,* fungi such as *Aspergillus niger* and *Chaetomium globosum.* For use, these compounds can be applied neat or employed in a diluted form. Satisfactory diluents include any inert material not destructive of the antimicrobial activity and especially liquid formulations comprising aqueous dispersions, solutions, and emulsions. Solid diluents include talc, corn starch, alumina and diatomaceous earth. The antimicrobial agents of this invention can also be deposed on materials such as natural fibers including paper, cotton, wool and synthetic fibers such as nylon, polypropylene, as well as upon inanimate surfaces including hard surfaces such as wood, glass, metal, tile, rubber, plastic, and porous surfaces such as concrete, leather and the like.

Briefly, the intermediate ketone I, 1,5-di-(3,3-dimethylnorborn-2-yl)-3-pentanone is reacted with ammonia, reduced, and then twice consecutively reacted with acrylonitrile and reduced. In addition, two subsidiary processes employ the alcohol and halide derivatives of ketone I. These are each separately reacted with 3,3'-iminobispropylamine to form the alkylated polyamine.

All of these processes can be appreciated in their broad scope by reference to Tables I, II, and III which present flow charts of the reactions set forth in greater detail below.

Generally all the reaction steps leading to the nitrile precursor to VIII,

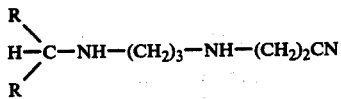

where R is

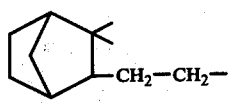

the reactions of Table I are set forth in the Examples. This same precursor can be obtained by the reactions of Table II and III and the details of the intermediate steps are straight-forward to one skilled in the art having the advantage of Tables II and III.

It should be helpful to state that Reactions 5 and 6 of Table II in the amination step (a) require more stringent reaction conditions than the reaction of ketone I and amine IV or ammonia V. It is helpful to conduct the reaction at temperatures of from 100° C. to 150° C. over a thoria oxide or other dehydrating catalyst.

Similarly, Reactions 8 and 9 in Table III in amination step (a) are conducted most suitably in a pressure vessel at temperatures of from 90° C. to 180° C. for chlorides IX and 40° C. to 180° C. for bromides IX.

In Reactions 4–9, the reactions can be performed neat or in a mutual solvent preferably an alcoholic solvent or a glycol of upwards to 20 carbon atoms. An excess of the indicated equimolar quantity of amines III or IV or ammonia V is highly desirable and most preferably at least a three-fold excess is employed.

As stated, the novel polyamine of this invention can be prepared by employing as a starting material either the ketone I, 1,5-di-(3,3-dimethylnorborn-2-yl)-3-pentanone; the alcohol II, 1,5-di-(3,3-dimethylnorborn-2-yl)-3-hydroxy pentane; or the halo IX preferably chloro, 1,5-di-(3,3-dimethylnorborn-2-yl)-3-halo pentane where halo is chloro, bromo, or iodo.

Ketone I is obtained by the free radical addition of acetic acid equivalent (anhydride preferably) to camphene to produce 3-(3,3-dimethylnorborn-2-yl)propionic acid which is in turn condensed to the ketone I as described in Examples A and B respectively.

Alcohol II is obtained by standard known synthetic routes such as the Meerwein-Poundorf-Verley reduction (Wilds in Adams, *Organic Reactions,* V. 2, N.Y., John Wiley & Sons, Inc., 1944, Chap. 5). Ketone I is heated with at least one equivalent of aluminum isopropoxide (⅓ mole of aluminum isopropoxide for each mole of ketone I in an excess of isopropyl alcohol. The reaction is carried out in a distillation column under slow distillation until no more acetone is detected in the distillate. Removal of the acetone, the lowest boiling component of the reaction mixture permits the reaction to proceed to completion. Sodium borohydride in alcohol is also useful.

Halo compound IX is likewise obtained by standard techniques by the halogenation of alcohol II, such for example by treatment with a hydrogen halide, a hydrogen halide in the presence of catalysts such as zinc chloride or sulfuric acid, phosphorous trihalide (iodo and bromo), phosphorous pentahalide, or phosphorous oxyhalide, i.e., $POCl_3$, thionyl halide.

Since the use of hydrogen halide can lead to possible mixtures of products, the use of other halogenating agents is preferred, and generally preferred are phosphorous tribromide, phosphorous triiodide, and phosphorous pentachloride or thionyl chloride. The reaction conditions and details are well known for such conversion of alcohols to halides and reference can be made to Noller and Dinsmore, *Organic Synthesis Cell,* V. 2, N.Y., John Wiley & Sons, Inc., 1943, p. 358, Goshorn, Boyd and Degering, *Organic Synthesis Cell,* V. 1, 2nd Ed., N.Y., John Wiley & Sons, Inc., 1941, p. 36, and Clark and Streight, *Trans Royal Society Canada,* V. 23, 77, 1929.

In employing ketone I as a starting material, reference can be made to the flow chart in Table I. Ketone I can be reacted either as in (1) with 3,3'-iminobispropylamine III, as in (2) with 1,3-diaminopropane IV, or as in (3) with ammonia. Referring to Table I, reaction routes (2) and (3) proceed through the common intermediate product VII to final product VIII.

Intermediate product VII is reacted with acrylonitrile and subsequently reduced to produce VIII. In general, the addition of the acrylonitrile is carried out by addition of small increments to an excess of the intermediate diamine VII.

It will be clear to one skilled in the art that other well known methods of primary amine synthesis from alcohols or the corresponding carbonium ion derived therefrom can also be employed. Such an example is the use of the Ritter reaction with a nitrile to provide the corresponding amide. This amide is in turn readily hydrolyzed in aqueous acid or alkali to the desired primary monoamine.

Returning now to the reduction of the precursor nitrile VIII, the reduction can be catalytic or chemical.

In such catalytic reductions, hydrogen saturates a precursor VIII (a) using agitation in the presence of the usual hydrogenation catalysts, such as transition metals and their reducible oxides. Especially effective catalysts are the noble metals and their oxides. A particularly preferred catalyst is platinum oxide. Generally, the hydrogenation reaction is carried out in a manner well known in the art at emperatures from ambient to 150° C. Small particles, e.g., 100–300 mesh of catalyst are admixed with the Schiff base and excess amine placed in a closed system pressurized with from 3–5 atmospheres of hydrogen gas. After reaction is complete, the pressure is released and the catalyst separated from the reaction mixture by filtration. The filtrate containing the polyamine VIII is then further purified by usual techniques. It is suitable for the reaction to be conducted neat, but more suitably a solvent such as $C_1$ to $C_{10}$ alcohols, $C_4$ to $C_{10}$ ethers, dioxane, and other inert solvents, i.e., those not irreversibly reactive to the reactants and products can be employed as such are commonly used in hydrogenation reactions. Preferably, whatever solvent may be present is removed under reduced pressure, the residue then dissolved in a suitable solvent, washed with water, followed by a further washing such as with a saturated aqueous sodium chloride solution. After drying, any remaining solvent can be removed by evaporation under reduced pressure giving the polyamine VIII usually as an oil. The polyamine may then be redissolved in loweralkanols, mixtures of loweralkanols and water diethylether, dioxane and then neutralized with an acid, e.g., hydrogen chloride, or neutralized directly with aqueous acids.

Acid addition salts are then isolated, if desired, by precipitation, evaporation or other usually employed techniques.

Suitable anions X for the salt I (a) include anions derived from inorganic acids, as well as those or organic acids such, for example, as halide, e.g., chloride, bromide or iodide or sulfate, bisulfate, nitrate, phosphate, acetate, propionate, maleate, succinate, laurate, oleate, palmitate, stearate, ascorbate, gluconate, citrate, carbonate, bicarbonate, benzoate, salicylate, pamoate, phthalate, furoate, picolinate, dodecylbenzenesulfonate, laurylethersulfate, nicotinate and the like. Generally, any anion derived from an acid is suitable and satisfactory when the polyamine salt anion $x^-$, e.g., chloride is to be replaced with other anions by well known anion exchange techniques.

In a chemically reductive procedure, the nitrile precursor to VIII is dissolved in an inert solvent especially a $C_1$ to $C_{10}$ alkanol or ether-type solvent and reacted with a chemical reductant such as sodium borohydride or lithium aluminum hydride, respectively.

Although as little as an eqvivalent of the chemical reductant can be used successfully, more satisfactory results are obtained if at least two molar excess or preferably at least a 2.5 molar excess of the chemical reductant is employed. After any initial reaction has subsided, the reaction mixture of precursor VIII and reductant may be heated at reflux for an hour or two, then cooled to room temperature, and afterwards concentrated under vacuum. The residue obtained is then further purified as by treatment with mineral acid or inorganic base as was described for polyamine VIII and the salt may thereafter be formed as previously described.

The 1-[1,5-di-(3,3-dimethylnorborn-2-yl)-3-pentyl]-1,5,9-triazanonane obtained in the several synthesis routes described herein may be in exo and endo isomer configurations and generally is a mixture of both. Many factors enter into the actual ratio of isomers formed and these can be temperature, solvents, steric effects, equilibration conditions, nature of substituents and others. However, it appears that the utility of the products of this invention is served without the necessity for strictly controlling the isomer composition. The content of a product mixture may be determined by vapor or liquid phase chromatography, NMR spectral analysis, fractional distillation and other methods. It is also possible to isolate pure isomers by selection of these and other separation techniques well known in the art.

The following specific examples are further illustrative of our invention, but should not be construed as any limitation on the processes herein described.

EXAMPLE A

Preparation of 3-(3,3-Dimethylnorborn-2-yl)propionic Acid

To refluxing acetic anhydride (1050 g., 10 moles), there is added dropwise over six hours a solution of camphene (136 g., 1 mole) and di-tert-butyl peroxide (0.1 mole, 14.6 g.). After complete addition, the mixture is heated at reflux for five hours. The cooled reaction mixture is concentrated under reduced pressure to leave a yellow-orange residual oil, 750 ml. of 2.5N NaOH is added to the residue which is then heated on the steam bath for one hour. The cooled solution is extracted once with ether, made acidic with concentrated HCl, and extracted thoroughly with ether. The dried ($Na_2SO_4$) ether extracts are concentrated under reduced pressure and the residue distilled under vacuum.

EXAMPLE B

Preparation of 1,5-Di-(3,3-Dimethylnorborn-2-yl)-2-pentanone 3-(3,3-Dimethylnorborn-2-yl)propionic acid (39 g., 0.20 mole) and iron (hydrogen reduced, 6.15 g., 0.11 mole) is heated for 1.5 hours at 195° C. under a nitrogen atmosphere. After that time, the temperature is increased to 290° C. and maintained at that temperature for three hours. The cooled reaction mass is extracted well with ether, filtered through Celite, and the ethereal extracts concentrated under vacuum. The residue is distilled and distilled under vacuum to give a more purified product.

EXAMPLE C

Preparation of 1,5-Di-(3,3-dimethylnorborn-2-yl)-3-pentanol

The ketone, 1,5-di-(3,3-dimethylnorborn-2-yl)-3-pentanone (2 grams) was dissolved in 100 ml. of ethanol and stirred with 2 grams of sodium borohydride overnight. The solvent was removed in vacuo and the residue partitioned between ethyl ether and water. The organic layer was dried over sodium sulfate. After filtration, and removal of solvent a colorless oil was obtained that crystallized on standing, m.p. 55° C.–56° C.

Analysis For $C_{23}H_{40}O$: Theoretical: C, 83.07; H: 12.12. Found: C, 82.50; H: 12.22.

EXAMPLE D

Preparation of 1,5-di-(3,3-dimethylnorborn-2-yl)-3-pentyl Chloride

A solution of 16.6 gm. of 1,5-di-(3,3-dimethylnorborn-2-yl)-3-pentanol in 25 ml. of dry pyridine is cooled to −10° C. There is then added with good agitation, 14.3 gm. of thionyl chloride over a 15 minute period. The solution is allowed to warm to room temperature and gradually heated over a period of 4 to 5 hours to 100° C. After an additional two hours at 100° C. the excess thionyl chloride is removed by vacuum stripping and the reside mixed with cracked ice. Three 100 ml. ether extractions are used to remove the halide, the diethyl ether extracts are washed with 4 × 200 ml. ice water, the ether layer separated, dried over anhydrous magnesium sulfate, filtered and stripped. The residue of di-substituted pentyl chloride may be further purified by distillation in vacuo or is suitable for further reaction as such.

EXAMPLE 1 — (Reaction 1a and 1b)

Preparation of 1-[1,5-Di-(3,3-dimethylnorborn-2-yl)-3-pentyl]-1,5,9-triazanonane Trihydrochloride 1,5-Di-(3,3-dimethylnorborn-2-yl)-3-pentanone (6.04 g., 0.02 mole) and 3,3'-iminobispropylamine (13.1 g., 0.10 mole) in 150 ml. toluene is heated at reflux overnight with a Dean-Stark water separator. The cooled solution is concentrated under reduced pressure. The residue is dissolved in ethanol and hydrogenated with PtO₂ at room temperature and 40 psi hydrogen pressure. The platinum catalyst is filtered off and the ethanol removed under vacuum. The residual oil is dissolved in ether and the ether solution washed several times with water to remove the excess 3,3'-iminobispropylamine. The ether extracts are dried over anhydrous sodium sulfate and concentrated under vacuum to leave the polyamine as a colorless oil (8.3 g., 100% yield).

The oil is dissolved in ether and hydrogen chloride gas is bubbled into the solution until no further pecipitation occurs. The ether is evaporated under reduced pressure to leave the product as a solid which is digested with hot isopropyl alcohol. The solids are collected by filtration and dried under vacuum at 70° C. to give a colorless product 10.8 g., (97%), m.p. 260° C.–262° C.

To a stirred solution of the amine (0.0065 mole) in anhydrous ether (100 cc. total volume) is added dropwise a solution of propionic acid (1.5 cc., 0.02 mole) in ether (10 cc.) over about 10 minutes. The resultant precipitate is aged, filtered, washed well with ether and dried to give 1-[1,5-di-(3,3-dimethylnorborn-2-yl)-3-pentyl]-1,5,9-triazanonane tripropionate, a white solid, m.p. 107.5° C.–109° C.

EXAMPLE 2 — (Reaction 2a and 2b)

Preparation of 1-[1,5-Di-(3,3-dimethylnorborn-2-yl)-3-pentyl]-1,5-diazapentane Via Direct Reaction 1,5-Di-(3,3-dimethylnorborn-2-yl)-3-pentanone (6.04 g., 0.02 mole) and 1,3-diaminopropane (0.10 mole) in 150 ml. toluene is heated at reflux overnight with a Dean-Stark water separator. The cooled solution is concentrated under reduced pressure. The residue is dissolved in ethanol and hydrogenated with PtO₂ at room temperature and 40 psi hydrogen pressure. The platinum catalyst is filtered off and the ethanol removed under vacuum. The residue is dissolved in ether and the ether solution washed several times with water to remove the excess 1,3-diaminopropane. The ether extracts are dried over anhydrous sodium sulfate and concentrated under vacuum to leave the diamine product, 1-[1,5-di-(3,3-dimethylnorborn-2-yl)-3-pentyl]-1,5-diazapentane.

EXAMPLE 3 — (Reactions 3a and 3b)

Preparation of 1-[1,5-Di-(3,3-dimethylnorborn-2-yl)-3-pentyl]amine

A mixture of 1,5-di-(3,3-dimethylnorborn-2-yl)-3-pentanone (16.5 g., 0.05 mole) and 30 g. of liquid ammonia in 100 ml. ethanol is hydrogenated for 12 hours at 130° C. and 1500 psi hydrogen pressure 4 g. Raney nickel catalyst. The catalyst is then filtered off and the ethanol removed under reduced pressure. The residue is dissolved in ether and the ether solution washed several times with 2.5N NaOH and then with water to remove the excess ammonia. The ether extracts are dried over anhydrous sodium sulfate and concentrated under vacuum to leave the product, 1-[1,5-di-(3,3-dimethylnorborn-2-yl)-3-pentyl]amine.

EXAMPLE 4 — (Reaction 3c and 3d)

Preparation of 1-[1,5-Di-(3,3-dimethylnorborn-2-yl)-3-pentyl]-1,5-diazapentane Via Acrylonitrile Route The product from Example 3, 1-[1,5-di-(3,3-dimethylnorborn-2-yl)-3-pentyl]amine, (11 g.) is dissolved in 20 ml. tert-butanol and chilled to 0° C. to 5° C. in an ice-water bath. Acrylonitrile (1.75 g., 2.2. ml., 0.033 mole) is added dropwise over a five minute period. The reaction mixture is allowed to warm to room temperature and is then heated at 60° C. overnight. The tert-butanol was removed under reduced pressure. The residual oil was dissolved in 150 ml. glacial acetic acid and hydrogenated with PtO₂ at room temperature and 40 psi hydrogen pressure. The platinum catalyst is filtered off and the acetic acid removed under vacuum. The residue is dissolved in ether and made basic with 10% sodium hydroxide. The ether solution is washed with water, dried over anhydrous sodium sulfate and concentrated under reduced pressure to leave the product, 1-[1,5-di-(3,3-dimethylnorborn-2-yl)-3-pentyl]-1,5-diazapentane.

EXAMPLE 5 — (Reactions 3e and 3f)

Preparation of 1-[1,5-di-(3,3-dimethylnorborn-2-yl)-3-pentyl]-1,5,9-triazanonane The product from Example 2 or Example 4 is dissolved in 20 ml. tert-butanol and chilled to 0° C. to 5° C. in an ice-water bath. Acrylonitrile (1.75 g., 2.2 ml., 0.033 mole) is added dropwise over a five minute period. The reaction mixture is allowed to warm up to room temperature and is then heated at 60° C. overnight. The tert-butanol was removed under reduced pressure. The residual oil was dissolved in 150 ml. glacial acetic acid and hydrogenated with $PtO_2$ at room temperature and 40 psi hydrogen pressure. The platinum catalyst is filtered off and the acetic acid removed under vacuum. The residue is dissolved in ether and made basic with 10% sodium hydroxide. The ether solution is washed with water, dried over anhydrous sodium sulfate and concentrated under reduced pressure to leave the product, 1-[1,5-di-(3,3-dimethylnorborn-2-yl)-3-pentyl]-1,5,9-triazanonane.

TABLE I

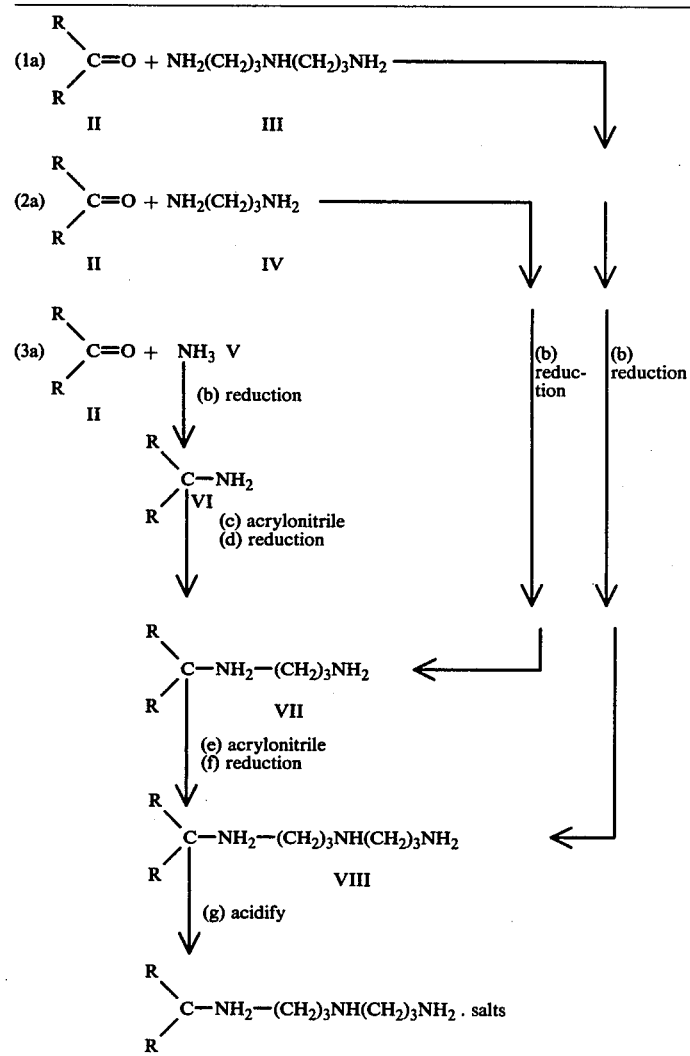

where R is as previously defined.

TABLE II

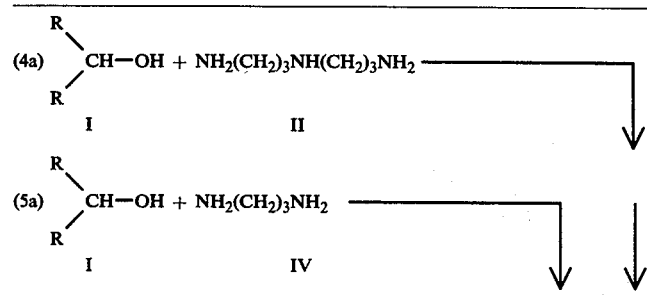

TABLE II-continued

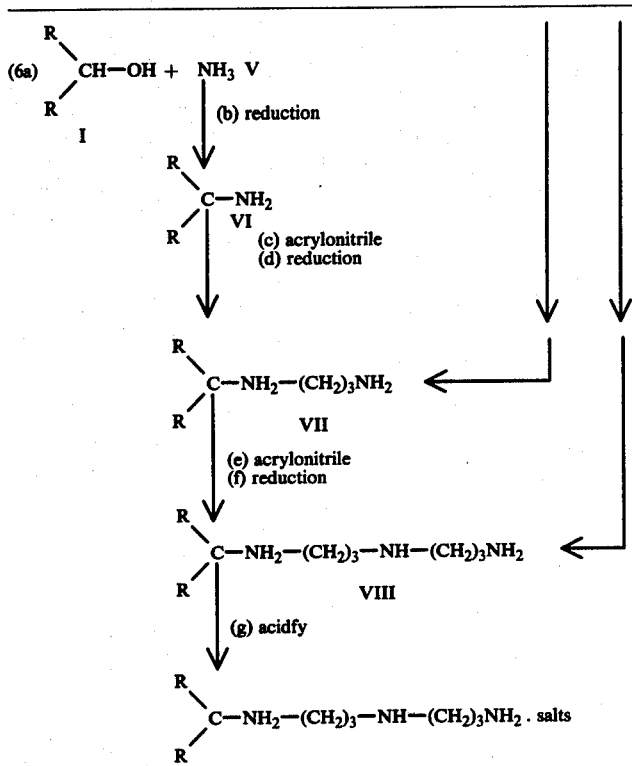

where R is as previously defined.

TABLE III

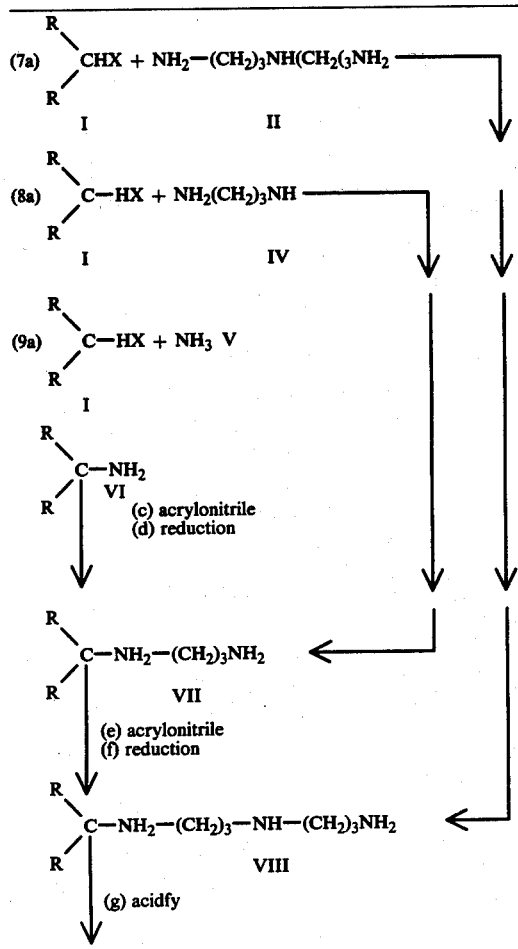

TABLE III-continued $$\begin{array}{c}R\\ \diagdown\\ C-NH_2-(CH_2(_3-NH-(CH_2)_3NH_2 \cdot salts\\ \diagup\\ R\end{array}$$

where R is as previously defined, and X is halide.

What is claimed is:

1. The compound

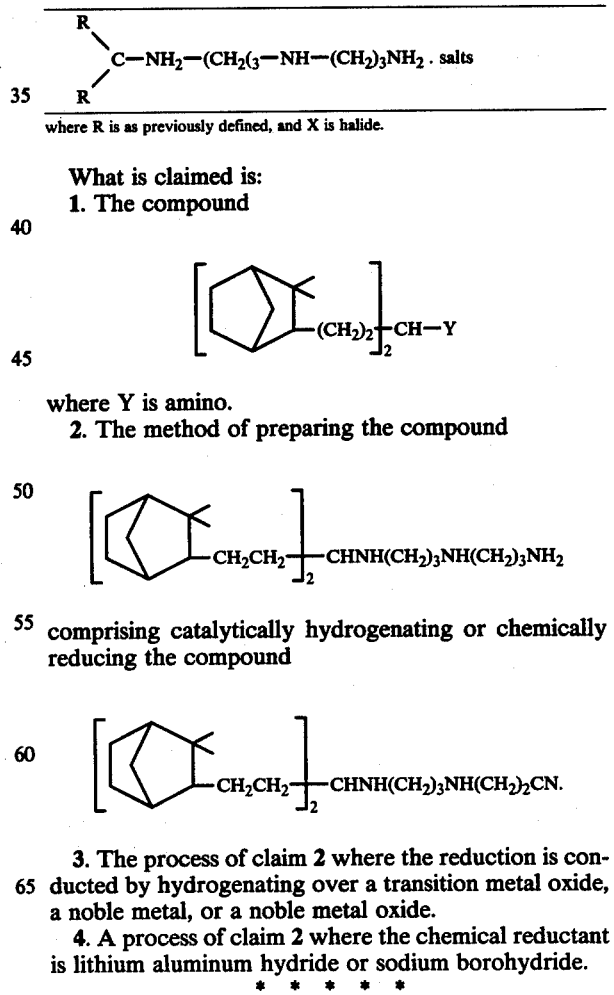

where Y is amino.

2. The method of preparing the compound $$\left[\underset{}{\text{norbornyl}}-CH_2CH_2-\right]_2 CHNH(CH_2)_3NH(CH_2)_3NH_2$$

comprising catalytically hydrogenating or chemically reducing the compound $$\left[\underset{}{\text{norbornyl}}-CH_2CH_2-\right]_2 CHNH(CH_2)_3NH(CH_2)_2CN.$$

3. The process of claim 2 where the reduction is conducted by hydrogenating over a transition metal oxide, a noble metal, or a noble metal oxide.

4. A process of claim 2 where the chemical reductant is lithium aluminum hydride or sodium borohydride.

* * * * *